(12) United States Patent
Karahalios et al.

(10) Patent No.: US 7,674,294 B2
(45) Date of Patent: Mar. 9, 2010

(54) END DEVICE FOR A VERTEBRAL IMPLANT

(75) Inventors: Dean G. Karahalios, Lake Forest, IL (US); Danny Horton Braddock, Jr., Germantown, TN (US); Andrew McCormick Dickson, Memphis, TN (US)

(73) Assignee: Warsaw Orthopedic, Inc.

( * ) Notice: Subject to any disclaimer, the term of this patent is extended or adjusted under 35 U.S.C. 154(b) by 693 days.

(21) Appl. No.: 11/291,419

(22) Filed: Dec. 1, 2005

(65) Prior Publication Data

US 2007/0162126 A1    Jul. 12, 2007

(51) Int. Cl.
*A61F 2/44* (2006.01)
(52) U.S. Cl. ................... 623/17.11; 623/17.15
(58) Field of Classification Search ... 623/17.11–17.16; 606/61, 63
See application file for complete search history.

(56) References Cited

U.S. PATENT DOCUMENTS

| | | | | |
|---|---|---|---|---|
| 2,864,446 | A | * | 12/1958 | Olson et al. ................ 83/610 |
| 3,102,671 | A | * | 9/1963 | Gershen ..................... 225/43 |
| 4,401,112 | A | | 8/1983 | Rezaian |
| 4,630,765 | A | * | 12/1986 | Samuelson et al. ........... 225/96 |
| 4,657,550 | A | | 4/1987 | Daher |
| 4,820,305 | A | | 4/1989 | Harms et al. |
| 4,932,975 | A | | 6/1990 | Main et al. |
| 5,026,373 | A | | 6/1991 | Ray et al. |
| 5,062,850 | A | | 11/1991 | MacMillan et al. |
| 5,133,980 | A | * | 7/1992 | Ream et al. .................. 426/115 |
| 5,336,223 | A | | 8/1994 | Rogers |
| 5,571,190 | A | | 11/1996 | Ulrich et al. |
| 5,571,192 | A | | 11/1996 | Schonhoffer |
| 5,609,635 | A | * | 3/1997 | Michelson .................. 623/17.16 |
| 5,702,451 | A | | 12/1997 | Biedermann et al. |
| 5,702,453 | A | | 12/1997 | Rabbe et al. |
| 5,702,455 | A | | 12/1997 | Saggar |
| 5,897,556 | A | | 4/1999 | Drewry et al. |
| 5,972,031 | A | * | 10/1999 | Biedermann et al. ......... 623/17.16 |
| 5,980,522 | A | | 11/1999 | Koros et al. |
| 5,989,290 | A | | 11/1999 | Biedermann et al. |
| 6,015,436 | A | | 1/2000 | Schonhoffer |
| 6,086,613 | A | | 7/2000 | Camino et al. |
| 6,190,413 | B1 | | 2/2001 | Sutcliffe |
| 6,193,755 | B1 | | 2/2001 | Metz-Stavenhagen et al. |
| 6,344,057 | B1 | | 2/2002 | Rabbe et al. |
| 6,682,561 | B2 | * | 1/2004 | Songer et al. ............. 623/17.11 |
| 6,682,562 | B2 | | 1/2004 | Viart et al. |
| 6,866,682 | B1 | * | 3/2005 | An et al. .................. 623/17.15 |
| 6,899,734 | B2 | | 5/2005 | Castro et al. |
| 6,929,662 | B1 | * | 8/2005 | Messerli et al. ............ 623/17.11 |
| 2004/0002761 | A1 | | 1/2004 | Rogers et al. |

FOREIGN PATENT DOCUMENTS

| | | |
|---|---|---|
| DE | 195 09 317 A1 | 9/1996 |
| FR | 2 636 227 | 3/1990 |
| WO | 0045751 | 8/2000 |
| WO | 2005070346 A1 | 8/2005 |

* cited by examiner

*Primary Examiner*—Pedro Philogene

(57) ABSTRACT

An end device attached to an implant and methods of use. The end device comprises a base having a receiving area, an opening, and at least one gate that is selectively positionable between open and closed orientations. The implant is sized to fit through the opening and into the receiving area when the gate is in the open orientation. Once inserted, the gate is sized to extend across at least a section of the opening and prevent the implant from escaping.

32 Claims, 4 Drawing Sheets

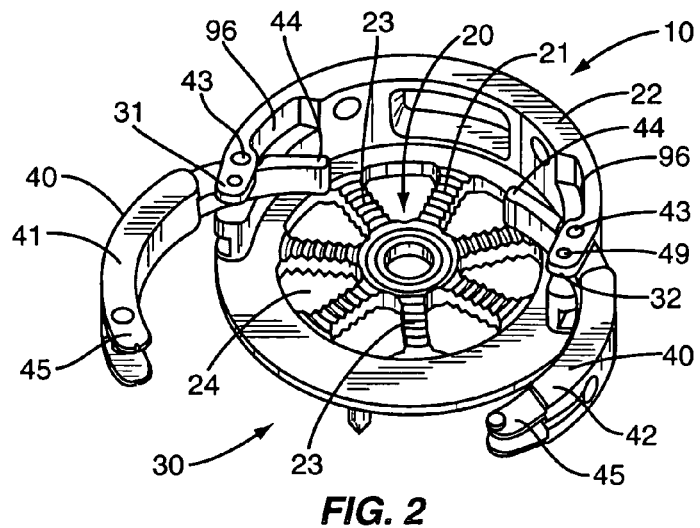
FIG. 2
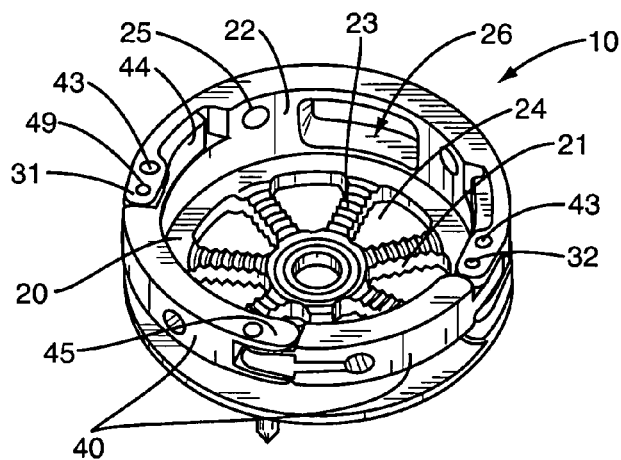
FIG. 3
FIG. 4

END DEVICE FOR A VERTEBRAL IMPLANT

BACKGROUND

Various procedures include removing the entirety or a section of a vertebral member. The procedures may also include removing more than one section or entirety of vertebral members. These procedures may be required due to damage to the vertebral member, such as that caused by a specific event such as trauma, a degenerative condition, a tumor, or infection.

Once the vertebral member is removed, an implant is inserted to replace the removed member or members. The implant maintains the spacing of the remaining vertebral members providing for them to function properly. The positioning and size of the implant are carefully determined prior to insertion. Once inserted, the implant should remain in position.

One surgical concern is securely interposing a vertebral implant between the remaining vertebral members to ensure that the implant can resist axial, torsional, and shear loading without causing anterior displacement ("kick-out"), posterior retropulsion of the implant and any associated graft material, or subsidence. Existing vertebral implants which attempt to minimize these methods of failure can often result in other undesirable consequences such as instrumentation pull-out, graft dislodgment, or erosion of nearby vascular and soft tissue structures due to high profile design.

SUMMARY

The present application is directed to devices and methods of an end device attachable to an implant. The end device comprises a base having a receiving area, an opening, and at least one gate that is selectively positionable between open and closed orientations. The implant is sized to fit through the opening and into the receiving area when the gate is in the open orientation. Once inserted, the gate is sized to extend across at least a section of the opening and prevent the implant from escaping.

BRIEF DESCRIPTION OF THE DRAWINGS

FIG. 2 is a perspective view of an end device in an open orientation according to one embodiment;

FIG. 3 is a perspective view of an end device in a closed orientation according to one embodiment;

FIG. 4 is a perspective view of a second side of the end device according to one embodiment;

DETAILED DESCRIPTION

Figure 1:
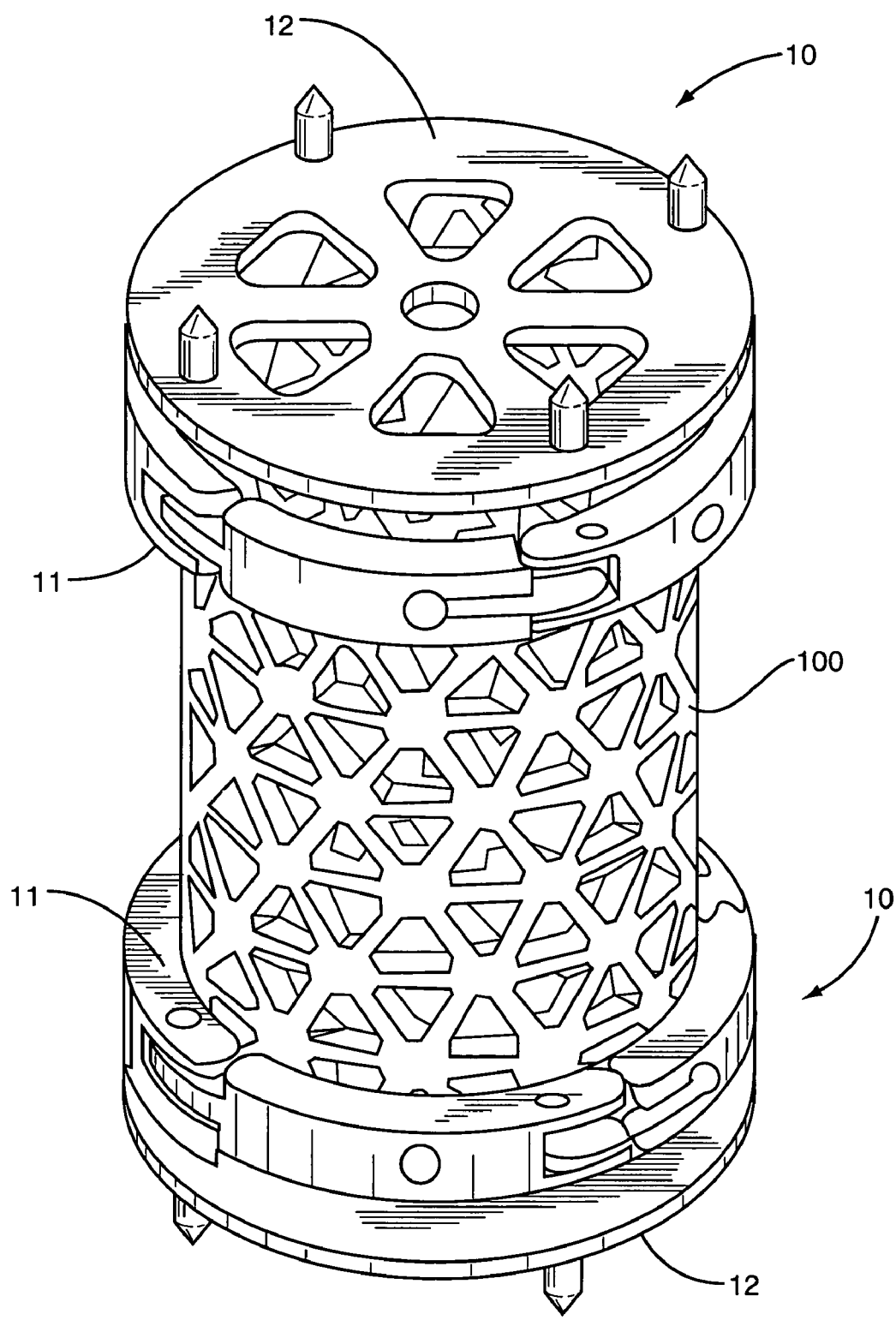
FIG. 1 is a perspective view of a pair of end devices mounted to an implant according to one embodiment.

FIG. 1 illustrates a pair of end devices, generally illustrated as element 10, each attached to one end of a vertebral implant 100. The end device 10 includes a first side 11 that faces towards the implant 100, and a second side 12 that faces towards a vertebral member. A receiving mechanism within the end device 10 is selectively positionable between open and closed orientations. The open orientation provides for inserting the implant 100 within a receiving area of the end device 10. The closed orientation prevents the implant 100 from being removed from the receiving area of the end device 10.

The term "implant" is used generally herein to describe a device that is inserted into a patient. Implant 100 may be inserted into a patient for a variety of purposes, and may have a variety of shapes and sizes. In the embodiment of FIG. 1, implant 100 has a cylindrical shape with a hollow interior for holding bone-growth material. One example of such a cylinder is disclosed in U.S. Pat. Nos. 5,897,556 and 6,149,651, which are incorporated herein by reference. The cylindrical body may comprise angled, intersecting elongate bars which form a plurality of triangular apertures. The cylindrical body defines a hollow bore configured to receive bone growth material.

FIGS. 2 and 3 illustrate the end device 10 with FIG. 2 illustrating an open orientation and FIG. 3 a closed orientation. An end device 10 is connected to the implant 100 and prevents subsidence, expulsion, and/or enables fusion. An implant 100 may be equipped with a single or multiple end devices 10. For implants 100 equipped with multiple end devices 10, the devices may be the same or different. In the embodiments of FIGS. 2 and 3, end device 10 includes a base 20, opening 30, and a gate 40. Base 20 includes a bottom 21 and a sidewall 22. A receiving area 26 is framed by the base 20 and gate 40 to receive the implant 100.

Bottom 21 shields the end members of the implant 100 from contacting the vertebral member. Bottom 21 may be constructed of supports 23 spaced apart with gaps 24 for bone growth material in the implant 100 to reach the vertebral member for bone and tissue ingrowth and vascularization. Supports 23 and gaps 24 may have a variety of shapes and sizes. The bottom 21 may further have a roughened surface to connect with the implant 100, such as when the implant 100 comprises a bone strut. Sidewalls 22 extend outward from the bottom 21 forming the receiving area 26. Sidewalls 22 may extend a variety of heights from the bottom 21 depending upon the context. Apertures 25 may extend through the sidewalls 22 and may be threaded to receive a fastener that connects the end device 10 to the implant 100. Apertures 25 also provide for the bone growth material to reach the vertebral member.

The outer surface of the bottom 21 is constructed to maintain the position relative to the vertebral member. As illustrated in FIG. 4, spikes 27 having a sharp tip may be positioned at spaced intervals to bite into the vertebral member. Ridges 28 may also be positioned along the surface to maintain the device position. The outer surface may also be roughened such as by a grit blast to further maintain the device position.

Opening 30 is positioned within the sidewall 22 and sized for the insertion of the implant 100. Opening 30 is defined between a first edge 31 and a second edge 32.

Gate 40 is selectively positionable between open and closed orientations for positioning and containing the implant 100 within the receiving area 26. Gate 40 comprises first member 41 and second member 42. Each of the members 41, 42 is movably connected to the sidewall 22 at a pivot 43. This connection provides for movement between the open orientation as illustrated in FIG. 2, and the closed orientation as illustrated in FIG. 3. Each member 41, 42 has an elongated shape having a first end 44 and a second end 45. Pivot 43 is positioned at a point intermediate between the ends 44, 45. In the open orientation, the first ends 44 are positioned within the receiving area 26 defined within the sidewalls 22. In the open orientation, a distance between the first ends 44 is less than a distance between the edges 31, 32. In the open orientation, the second ends 45 are spaced away from the opening 30 with a distance between the second ends 45 being greater than the distance between the edges 31, 32. The extent of pivoting may vary depending upon the application. In one embodiment, the gates 40 have a swing of about 50° between the open and closed orientations.

Members 41, 42 have an arcuate shape that matches the sidewalls 22 and extends around the periphery of the bottom 21 when in the closed orientation. In the embodiment of FIG. 3, members 41, 42 have a length for the ends 45 to be in an overlapping configuration when in the closed orientation. One or both ends 45 may include a lock mechanism to maintain the members 41, 42 in the closed orientation. In the embodiment of FIGS. 2 and 3, the lock mechanism includes a ball and detent combination that mates together in the closed orientation. First and second edges 31, 32 of the sidewalls may further include a locking mechanism that engages the members 41, 42. In one embodiment, each edge 31, 32 includes an indent or aperture 49 that receives a mating tab located on the members 41, 42 to further secure the members 41, 42 in the closed orientation. A deformable spring interface and a fastener may also be used to keep the gate in the closed orientation.

Figure 5:
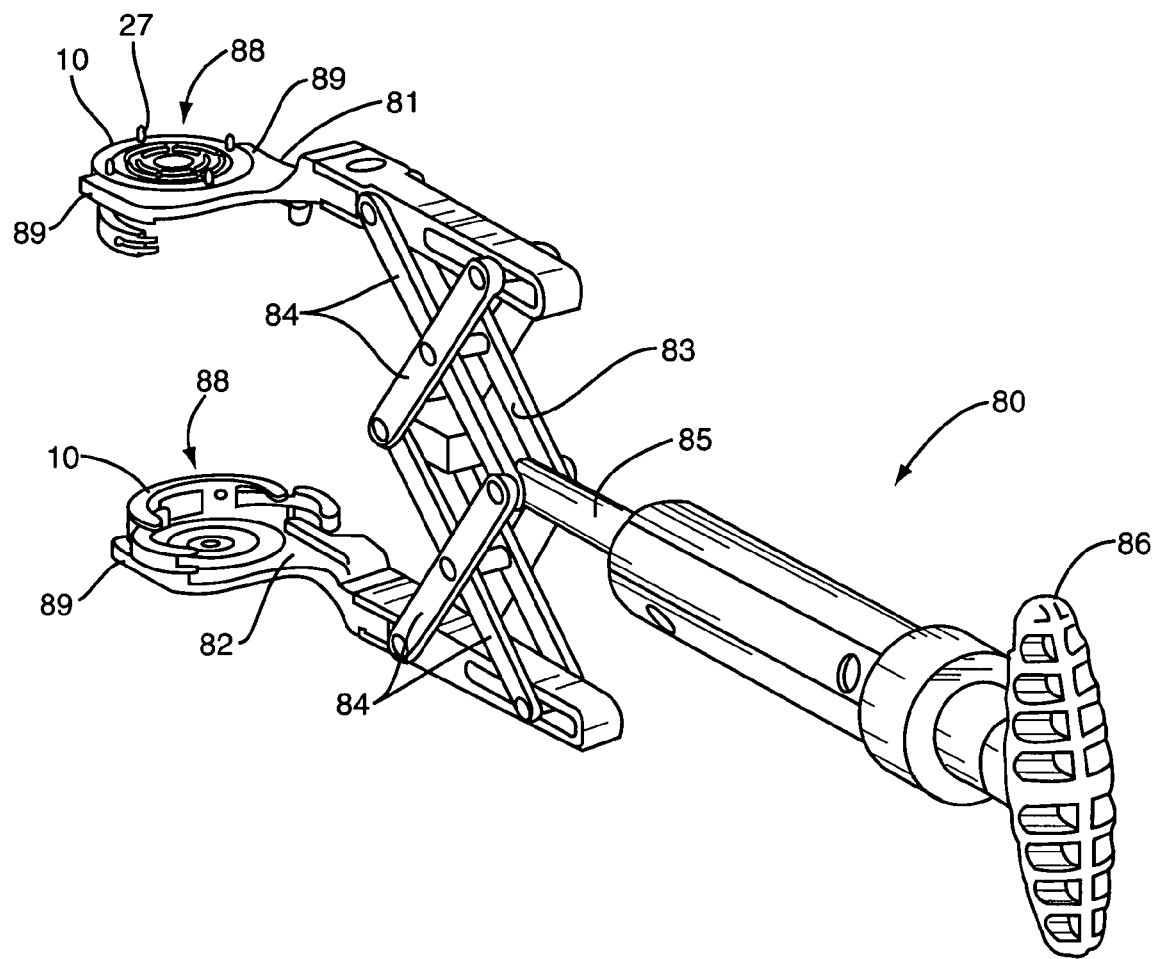
FIG. 5 is a perspective view of a pair of end devices mounted to an insertion device according to one embodiment.

Members 41, 42 may have the same or different height relative to the sidewalls 22. In the embodiments of FIGS. 2 and 3, members 41, 42 have a smaller height and are spaced upward from the bottom 21 with an upper edge of the members 41, 42 substantially matching an upper edge of the sidewalls 22. This gap between the members 41, 42 and the bottom 21 forms a space for the insertion device 80 as illustrated in FIG. 5.

Insertion device 80 is constructed to position the devices 10 relative to the vertebral members. Device 80 includes first and second arms 81, 82 each sized to hold an end device 10. Each arm 81, 82 has spaced-apart fingers 89 forming a capture area to receive the end devices 10. The fingers 89 form an opening 88 sized to slide the end devices 10 into the capture area. An adjustment mechanism 83 controls the distance between the arms 81, 82. In this embodiment, adjustment mechanism 83 is a jack device having pivoting linkages 84 attached to an arm 85. Handle 86 is operatively connected to the arm 85 to control the movement of the linkages 84 and thus the relative spacing of the arms 81, 82.

In use, one or two end devices 10 are slid through the openings 88 formed by the fingers 89 on the arms 81, 82. The end devices 10 are positioned in the capture area defined by the arms 81, 82 with the spikes 27 extending outward in preparation for positioning within the vertebral members. Further, the gates 40 are in the open orientation.

With the end devices 10 attached, the arms 81, 82 are positioned in a relatively closed orientation and are spaced apart a distance to fit between the remaining vertebral members. The surgeon then manipulates the handle 86 to insert the arms 81, 82 with the end devices 10 between the vertebral members. Once inserted, handle 86 is rotated to move apart the arms 81, 82. This movement causes the spikes 27 to be driven into the vertebral members to attach the end devices 10. The expansion movement may also distract the vertebral members.

With the end devices 10 in the open orientation, the implant 100 is moved through the gates 40 and into the receiving area 26. The gates 40 in the open orientation retract the soft tissue that may surround the vertebral members and keep open the line of sight for the surgeon. Once the end devices 10 are inserted, the implant 100 is inserted through the opening 30 and contacts the first ends 44 of the arms 41, 42. Further insertion of the implant 100 into the receiving area 26 causes the arms 41, 42 to move about their respective pivots 43 towards the closed orientation. In one embodiment, complete insertion of the implant 100 into the receiving area 26 results in the arms 41, 42 becoming locked together. In another embodiment, the surgeon locks the arms 41, 42 together after the insertion of the implant 100.

Once the implant 100 and end devices 10 are inserted, the insertion device 80 is removed from the end devices 10. The opening 88 in the arms 81, 82 is aligned facing away from the handle 86. The surgeon manipulates the handle 86 and pulls the insertion device 80 in a proximal direction thus causing the end devices 10 and implant to slide out of the fingers 89 and remain between the vertebral members.

The embodiments illustrated in FIGS. 2 and 3 include a gate 40 having first and second members 41, 42. Gate 40 may further comprise a single member that extends across the opening 30 to prevent escape of the implant 100. Both the single gate and multiple gate embodiments may extend across the entirety or a portion of the opening 30. The embodiment of FIGS. 2 and 3 illustrate the first and second members 41, 42 extending across the entirety of the opening 30. Other embodiments include the gate 40 being smaller than the opening leaving a gap that is of a smaller size than the implant 100 thus preventing escape.

Figure 6:
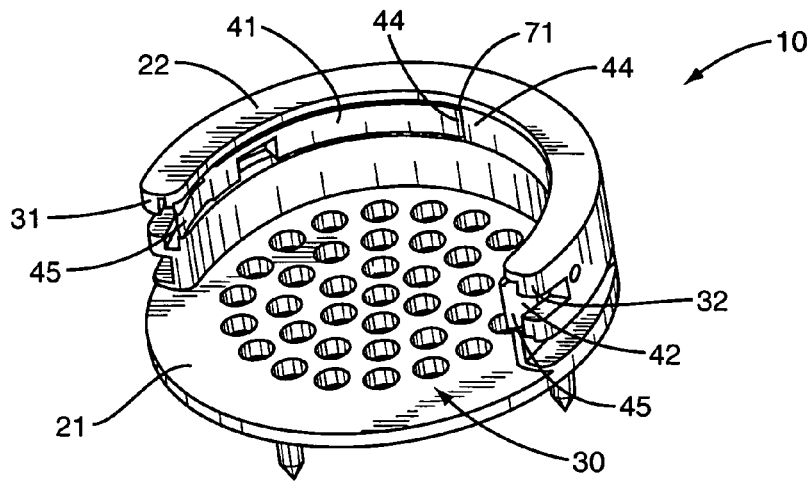
FIG. 6 is a perspective view of an end device having a sliding gate in an open orientation according to one embodiment.
Figure 7:
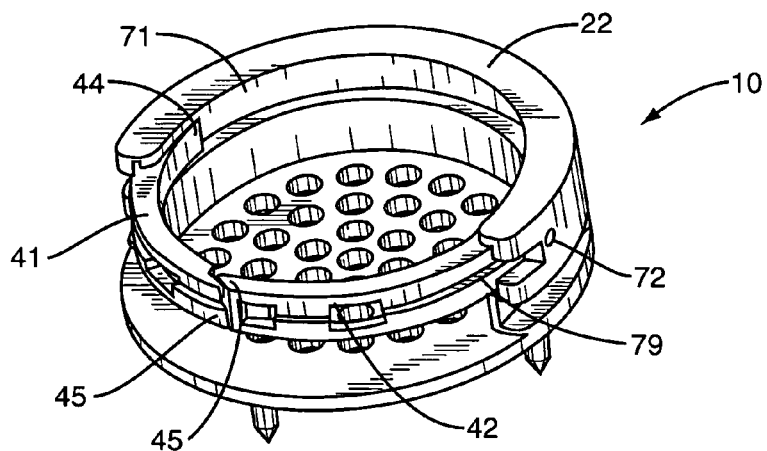
FIG. 7 is a perspective view of an end device having a sliding gate in a closed orientation according to one embodiment.

Another embodiment of a gate 40 features a sliding attachment with the base 20. As illustrated in FIGS. 6 and 7, sidewalls 22 include a slot 71 within an inner face. First and second members 41, 42 are sized to slide within the slot between an open orientation as illustrated in FIG. 6, and a closed orientation as illustrated in FIG. 7. Slot 71 may extend around the entirety of the sidewall 22, or a limited section adequate to receive the members 41, 42 an amount to clear the opening 30 for insertion of the implant 100. In the embodiment of FIG. 6, the first ends 44 of the members 41, 42 make contact in the open orientation with the second ends 45 being within the sidewalls 22. In the closed orientation, second ends 45 are in contact. Members 41, 42 may be attached within the sidewall 22 to prevent full removal. In one embodiment as illustrated in FIG. 7, pins 72 within the sidewall 22 are positioned within a groove 79 in the members 41, 42 to prevent the complete removal.

In other embodiments of this sliding arrangement, first ends 44 may be spaced apart in the open orientation, and second ends 45 may not be in contact in the closed orientation. In another embodiment, multiple members may be used, as opposed to the single member configuration illustrated in FIGS. 6 and 7. In another embodiment, slot 71 for receiving the members 41, 42 is positioned on an outer face of the sidewall 22.

Figure 8:
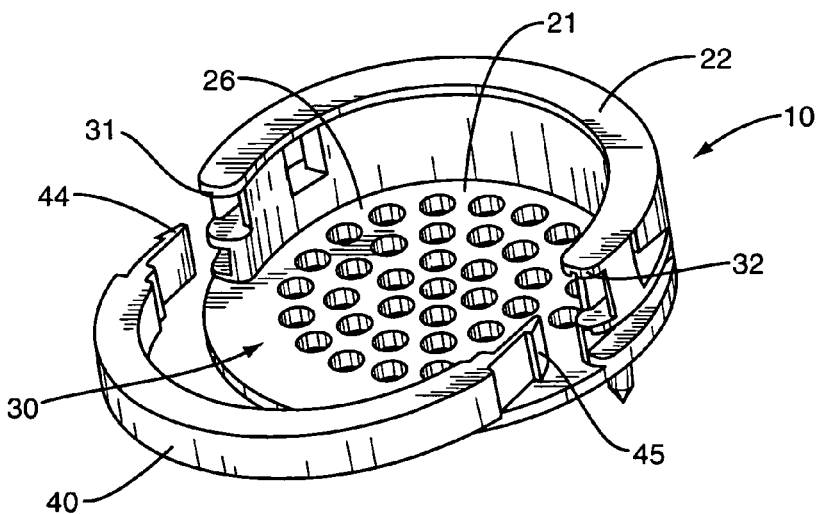
FIG. 8 is a perspective view of a removable gate according to one embodiment.

FIG. 8 illustrates another embodiment having a removable gate 40. Gate 40 includes first and second ends 44, 45 each having a locking mechanism that engages first and second edges 31, 32 of the sidewall 22. In the open orientation, gate 40 is removed allowing for the implant to be inserted through the opening 30 into the receiving area 26. In the closed orientation, gate 40 is mounted to the sidewalls 22 thereby enclosing the receiving area 26 and preventing escape of the implant 100. In another embodiment (not illustrated), the removable gate 40 is comprises of two or more sections. Each of the sections is separately removable from and attachable to the sidewalls.

In embodiments having a pivoting gate as illustrated in FIGS. 2 and 3, pivot 43 may be positioned at a variety of locations along the gate. In the embodiments of FIGS. 2 and 3, pivot 43 is positioned between the first and second ends 44, 45. In another embodiment, pivot 43 is positioned at the first end 45.

End device 10 may further include a combination of different gate configurations. By way of example, one section of the gate 40 may have a pivoting configuration, with a second section having a sliding or removable configuration. In one embodiment, gate 40 is configured for both sliding and pivoting.

In one embodiment of a pivoting gate as illustrated in FIGS. 2 and 3, one or both members 41, 42 have a tapered width that increases from the first end 44 towards the second end 45. Sidewall 22 includes a cutout section 96 into which the first end 44 is inserted when the gate 40 moves to the closed orientation. Cutout section 96 has a constant width. A section of the width of the members 41, 42 is slightly greater than the width of the cutout section 96. This causes the members 41, 42 to become slightly wedged into the cutout section 96 in the open orientation to maintain the members 41, 42 in the open orientation. The differences in widths between the cutout section 96 and the members 41, 42 is only slight thus not greatly increasing the amount of force required to move the move the members 41, 42 to the closed orientation. In another embodiment, the width of the members 41, 42 is constant and the cutout section 96 has a tapering width. In another embodiment, a ball detent mechanism is used to maintain one or both members 41, 42 in the open orientation.

A spacing device (not illustrated) may be positioned on a second side 12 of the end device 10. The spacing device may have an angled shape such that the end device 10 with implant 100 corresponds to the curvature of the spine. The spacing device may be separately attached to the bottom surface, or may be integral with the bottom surface.

The term "distal" is generally defined as in the direction of the patient, or away from a user of a device. Conversely, "proximal" generally means away from the patient, or toward the user. Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting.

The present invention may be carried out in other specific ways than those herein set forth without departing from the scope and essential characteristics of the invention. In one embodiment, bottom 21 of base 20 is solid. In another embodiment, the supports 23 are deleted, and the bottom 21 of the base 20 is open, with only a rim remaining to support the implant 100. In another embodiment, supports 23 are removable, and connect to the bottom 21 as a separate element intended to contain bone fusion material. The individual members 41, 42 may have the same or different sizes and shapes. In one embodiment, sidewall 22 is positioned inward from an outer edge of the bottom 21. The present embodiments are, therefore, to be considered in all respects as illustrative and not restrictive, and all changes coming within the meaning and equivalency range of the appended claims are intended to be embraced therein.

What is claimed is:

1. An end device for a vertebral implant comprising:
    a base having a bottom and a sidewall that extends from the bottom to form a receiving area;
    an opening in the sidewall that leads into the receiving area;
    a gate having a first end and a second end and a bottom surface and a top surface, the gate being attached to the sidewall and selectively positionable between an open orientation with the second end positioned clear of the opening and a closed orientation with the second end positioned at the opening with the gate extending across a section of the opening to prevent the implant from escaping from the receiving area, the top surface of the gate facing away from the bottom of the base when the gate is in the closed orientation;
    the gate configured with the top surface of the gate that is in the opening being exposed when the gate is in the closed orientation; and
    spikes that extend outward from a second face of the bottom.

2. The device of claim 1, wherein the gate is pivotally attached to the sidewall at a point between the first end and the second end.

3. The device of claim 2, wherein the gate is attached to the sidewall at a point in closer proximity to the first end than to the second end.

4. The device of claim 2, wherein the first end extends into the receiving area when the gate is in the open orientation.

5. The device of claim 1, wherein the gate is removed from the sidewall in the open orientation.

6. The device of claim 1, further comprising a second gate attached to the sidewall and selectively positionable relative to the base.

7. The device of claim 1 wherein the bottom extends through the opening such that the second end of the gate extends over the base toward a direction that the sidewall extends from the bottom of the base.

8. The device of claim 1 wherein the gate further comprises a portion medial between said first and second ends, and wherein that portion overlaps the base, when the gate is in the second orientation, when viewed from a direction that the sidewall extends from the bottom of the base.

9. An end device for a vertebral implant comprising:
    a base having a bottom and a sidewall that extends from the bottom to form a receiving area;
    an opening in the sidewall that leads into the receiving area, the opening extending between first and second edges of the sidewall;
    a first gate mounted to the first edge and sized to extend across a first section of the opening; and
    a second gate mounted to the second edge and sized to extend across a second section of the opening;
    the first and second gates being positionable between a first orientation with the first and second gates positioned clear of the opening, and a second orientation with the first and second gates positioned across at least a section of the opening.

10. The device of claim 9, wherein each of the first and second gates are pivotally attached to the sidewall at a point between first and second ends.

11. The device of claim 10, wherein the first ends are positioned within the receiving area when the first and second gates are in the first orientation, and aligned with the sidewall in the second orientation.

12. The device of claim 9, wherein the first and second gates are substantially the same length.

13. The device of claim 9, wherein second ends of the first and second gates comprises a locking mechanism to maintain the gates in the closed orientation.

14. The device of claim 9, wherein second ends of the first and second gates are spaced apart in the closed orientation.

15. The device of claim 9, wherein second ends of the first and second gates are positioned outside of the first and second edges of the sidewall in the open orientation, and aligned with the first and second edges in the closed orientation.

16. The device of claim 9, wherein a distance between second ends of the gates in the open orientation is greater than a width of the opening.

17. The device of claim 9, further comprising supports that are spaced apart to form gaps within the bottom.

18. The device of claim 9, further comprising slots within the sidewall to house the first and second gates in the open orientation.

19. The device of claim 9, wherein the first and second gates are unmounted from the first and second edges of the sidewall in the open orientation.

20. An end device for an implant comprising:
a base having a receiving area to house the implant, the base further having a bottom with a surface that faces into the receiving area;
an opening within the base that leads into the receiving area;
both the opening and the receiving area being open opposite from the bottom; and
a gate mounted to the base;
the gate being positionable between a first orientation positioned clear of the opening to insert the implant within the receiving area, and a second orientation with the gate positioned across at least a section of the opening to maintain the implant within the receiving area;
the base including a bottom surface with at least one gap therethrough, the base substantially peripherally surrounding the gap.

21. An end device for an implant comprising:
a base having a receiving area to house the implant;
an opening within the base that leads into the receiving area; and
a gate mounted to the base;
the gate being positionable between a first orientation positioned clear of the opening to insert the implant within the receiving area, and a second orientation with the gate positioned across at least a section of the opening to maintain the implant within the receiving area;
a slot within the base to receive the gate when positioned in the first orientation;
the opening being configured for a top side of a section of the gate that is positioned in the opening to be exposed when the gate is in the second orientation.

22. The device of claim 21, wherein the gate is pivotally mounted to the base.

23. The device of claim 21, wherein the gate is removably attached to the base, the gate comprises first and second ends each having locking mechanisms that attach to the base.

24. The device of claim 21, wherein the gate extends across an entirety of the opening in the second orientation.

25. The device of claim 21, wherein the gate comprises first and second sections that each extend across at least a portion of the opening in the second orientation.

26. A method of attaching an end device to a vertebral implant, the method comprising the steps of:
positioning a gate away from an opening to a first orientation;
receiving the implant through the opening and into a receiving area;
contacting a first section of a gate with the implant, the first section disposed in the receiving area, to thereby cause the gate to move from the first orientation to a second orientation across at least a section of the opening and maintaining the implant within the receiving area.

27. The method of claim 26, wherein the step of moving the gate from the first orientation to a second orientation comprises pivoting the gate about a pivot from the first orientation to the second orientation.

28. The method of claim 26, further comprising inserting spikes positioned on a second side of the receiving area into a vertebral member.

29. A method of attaching an end device to a vertebral implant, the method comprising the steps of:
positioning a gate away from an opening to a first orientation;
receiving the implant through the opening and into a receiving area;
moving the gate from the first orientation to a second orientation across at least a section of the opening and maintaining the implant within the receiving area;
wherein the step of moving the gate from the first orientation to a second orientation comprises sliding the gate along a base member from the first orientation to the second orientation with a top surface of the gate positioned away from a bottom of the opening being exposed when the gate is in the second orientation.

30. A method of attaching an end device to a vertebral implant, the method comprising the steps of:
positioning first and second gates in an open orientation with outer ends positioned away from an opening;
inserting the implant through the opening;
moving the implant into a receiving area and contacting inner ends of the first and second gates; and
moving the implant into a receiving area and simultaneously moving the first and second gates towards a closed orientation.

31. The method of claim 30, further comprising locking the first and second gates in the closed orientation.

32. The method of claim 30, further comprising attaching the end device within a vertebral member with the receiving area adjacent to the vertebral member.

* * * * *